United States Patent
Carraro et al.

(10) Patent No.: US 9,931,655 B2
(45) Date of Patent: Apr. 3, 2018

(54) MODULE FOR DISPENSING A PRODUCT INTENDED TO BE MOUNTED ON A PRESSURIZED SUPPLY DUCT FOR SAID PRODUCT

(71) Applicant: ALBEA LE TREPORT, Le Treport (FR)

(72) Inventors: Daniel Carraro, Asnières-sur-Seine (FR); Sylvain Defert, Saint-Ouen L'Aumône (FR)

(73) Assignee: ALBEA LE TREPORT, Le Treport (FR)

( * ) Notice: Subject to any disclaimer, the term of this patent is extended or adjusted under 35 U.S.C. 154(b) by 0 days.

(21) Appl. No.: 15/126,479

(22) PCT Filed: Mar. 25, 2015

(86) PCT No.: PCT/EP2015/056480
§ 371 (c)(1),
(2) Date: Sep. 15, 2016

(87) PCT Pub. No.: WO2015/155015
PCT Pub. Date: Oct. 15, 2015

(65) Prior Publication Data
US 2017/0080442 A1 Mar. 23, 2017

(30) Foreign Application Priority Data

Apr. 8, 2014 (FR) ...................................... 14 53116

(51) Int. Cl.
*B67D 7/76* (2010.01)
*B05B 11/04* (2006.01)
(Continued)

(52) U.S. Cl.
CPC ............ *B05B 11/047* (2013.01); *A01N 25/10* (2013.01); *A01N 31/16* (2013.01); *A01N 59/16* (2013.01);
(Continued)

(58) Field of Classification Search
CPC ....... B05B 11/047; B05B 11/30; B65D 35/38; B65D 47/24
(Continued)

(56) References Cited

U.S. PATENT DOCUMENTS

| | | | |
|---|---|---|---|
| 5,909,959 A * | 6/1999 | Gerich | B01F 5/0615 222/459 |
| 2002/0005412 A1* | 1/2002 | Laforcade | B01F 3/0861 222/129 |

(Continued)

FOREIGN PATENT DOCUMENTS

| | | |
|---|---|---|
| GB | 2470615 A | 12/2010 |
| WO | 2012/013894 A1 | 2/2012 |
| WO | 2012/084557 A1 | 6/2012 |

OTHER PUBLICATIONS

WO 2012084557 Machine Translation; Machine Translation from "www.wipo.int".*

(Continued)

*Primary Examiner* — Jeremy W Carroll
(74) *Attorney, Agent, or Firm* — Banner & Witcoff, Ltd.

(57) ABSTRACT

A module for dispensing a product intended to be mounted on a conduit (4) for pressurized supply of the product. The module has a path (2) for retrieving the product from a supply passage (5) which is intended to be in communication with the conduit to a passage (3) for discharging the product for the dispensing thereof. The retrieval path having at least one downstream conduit that opens into the discharge passage (3) and at least one upstream conduit that is
(Continued)

in communication with the supply passage (5). The upstream and downstream conduits having a U-shaped junction that is designed to place the conduits in communication. At least one of the conduits being delimited by at least one wall that is capable of providing a microbiocidal action on the product contained in the conduit.

13 Claims, 5 Drawing Sheets

(51) Int. Cl.
    *B05B 11/00*     (2006.01)
    *B65D 47/24*     (2006.01)
    *B65D 35/38*     (2006.01)
    *A01N 25/10*     (2006.01)
    *A01N 31/16*     (2006.01)
    *A01N 59/16*     (2006.01)
    *A61L 2/08*     (2006.01)
    *A61L 2/16*     (2006.01)

(52) U.S. Cl.
    CPC ............... *A61L 2/08* (2013.01); *A61L 2/16* (2013.01); *B05B 11/0067* (2013.01); *B05B 11/04* (2013.01); *B05B 11/30* (2013.01); *B65D 35/38* (2013.01); *B65D 47/24* (2013.01)

(58) Field of Classification Search
    USPC .................. 222/190, 484, 485, 521, 547
    See application file for complete search history.

(56) References Cited

U.S. PATENT DOCUMENTS

| | | |
|---|---|---|
| 2007/0194149 A1 | 8/2007 | Mavrakis et al. |
| 2010/0308136 A1* | 12/2010 | Songbe ............... B05B 1/3436 239/492 |
| 2013/0140225 A1 | 6/2013 | Decock et al. |
| 2015/0166224 A1* | 6/2015 | Greiner-Perth .... B65D 47/2068 222/153.06 |

OTHER PUBLICATIONS

Jun. 16, 2015—Translated International Search Report of PCT/EP2015/056480.

* cited by examiner

US 9,931,655 B2

MODULE FOR DISPENSING A PRODUCT INTENDED TO BE MOUNTED ON A PRESSURIZED SUPPLY DUCT FOR SAID PRODUCT

CROSS-REFERENCE TO RELATED APPLICATIONS

The present application is a U.S. National Phase filing of International Application No. PCT/EP2015/056480, filed on Mar. 25, 2015, designating the United States of America and claiming priority to French Patent Application No. 1453116 filed Apr. 8, 2014. The present application claims priority to and the benefit of all the above-identified applications, which are all incorporated by reference herein in their entireties.

The invention relates to a module for dispensing a product and to a container comprising a reservoir in which a product is intended to be packaged, said container having a conduit for pressurised supply of said product and, mounted on said conduit, such a dispensing module.

In a particular application, the product is of the lotion, gel or cream type, for example for cosmetic use or for pharmaceutical treatments.

The dispensing module may comprise a cap that is mounted on a base, forming a path therebetween for retrieving the product from a supply passage which is intended to be in communication with the supply conduit to a passage for discharging said product for the dispensing thereof, for example in a small amount or as a continuous stream.

According to one embodiment, the module is supplied with pressurised product by reversible manual deformation of the reservoir, for example in the form of a flexible tube. According to another embodiment, the module is of the push-button type for actuating the movement of the supply conduit of a pump over a stroke for dispensing/suction of the pressurised product.

Throughout the world, various directives aim to regulate, control and limit the presence of substances that are potentially hazardous for human health in products, in particular cosmetic products. One of them is the European REACH (Registration, Evaluation and Authorisation of Chemicals) directive. Thus an environmental trend is driving cosmetics manufacturers to limit or even eliminate from their formulas preservatives that are often the cause of allergies or intolerances.

Cosmetic products are therefore becoming more and more fragile. In particular, it is difficult for them to withstand mechanical or thermal stress (causing for example phase separation) and contact with air (causing for example drying out or oxidation) and can easily be contaminated by bacteria and fungi.

To combat contamination, formulators attempt to reinforce the intrinsic preservative activity of their products by adding ingredients having a preservative activity, such as certain essential oils, essences of orange, vitamin C, etc. that are not declared as preservatives. They also limit the free activity of water, which they attempt to keep low (AW<0.6) so that bacteria develop to little or no extent.

At the same time, both with regard to the reservoir in which the product is packaged and with regard to the dispensing module, protective containers are appearing on the market. In particular, the containers have to prevent microbiological contamination of the product, not only during storage but especially between two uses, and in particular by back-contamination from the discharge passage towards the inside of the reservoir by means of the retrieval path.

To do this, complex and expensive dispensing modules have been proposed, the high level of antimicrobial protection of which is not always essential, in particular when the product itself has an intrinsic preservative activity.

The invention aims to improve the prior art by proposing in particular a dispensing module having a simple design in which the retrieval of the product is ensured while preventing the microbial contamination thereof between two uses, in particular by back-contamination from the discharge passage to the inside of the reservoir.

For this purpose, according to a first aspect, the invention proposes a product-dispensing module which is intended to be mounted on a conduit for pressurised supply of said product, said module having a path for retrieving the product from a supply passage which is intended to be in communication with said conduit to a passage discharging said product for the dispensing thereof, said retrieval path having at least one downstream conduit that opens into the discharge passage and at least one upstream conduit that is in communication with the supply passage, the upstream and downstream conduits having a U-shaped junction that is arranged so as to place said conduits in communication, at least one of said conduits being delimited by at least one wall that is capable of providing a microbiocidal action on the product contained in said conduit.

According to a second aspect, the invention proposes a container comprising a reservoir in which a product is intended to be packaged, said container having a conduit for pressurised supply of said product and, mounted on said conduit, such a dispensing module.

Other objects and advantages of the invention will become apparent in the following description, given with reference to the accompanying drawings, in which.

Figure 1:
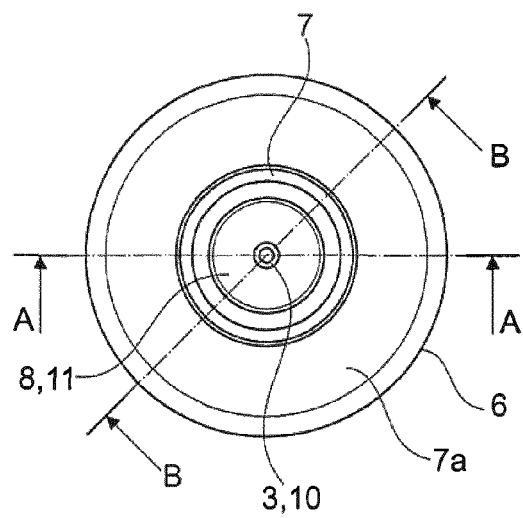
FIG. 1 is a plan view of a container according to an embodiment of the invention.
Figure 1A:
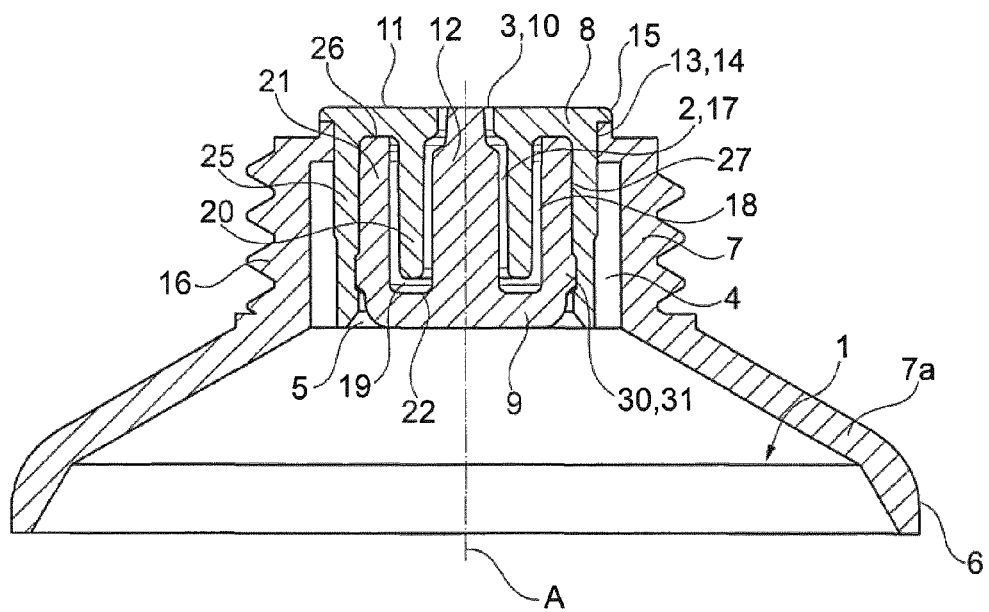
FIG. 1a is partial cross section along the line AA of the container in FIG. 1.
Figure 1B:
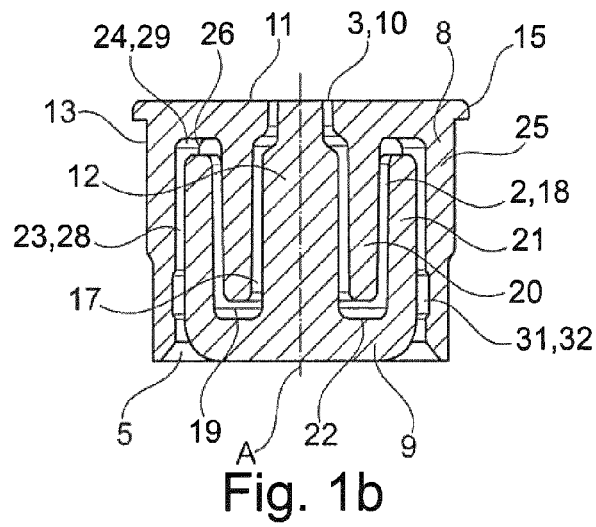
FIG. 1b is a cross section along the line BB of the dispensing module of the container in FIG. 1.

In the description, the terms for positioning in space are taken with reference to the upright position of the dispensing module and of the reservoir as shown in FIGS. 1a, 5a and 6 to 8.

In relation to the drawings, a container is described comprising a reservoir 1 in which a product is intended to be packaged. In an example of an application, the product is a lotion, a gel or a cream, for cosmetic use or for pharmaceutical treatments.

The container is equipped with a module for dispensing the product packaged in the reservoir 1, said module having a path 2 for retrieving said product from said reservoir as far as a discharge passage 3 for the dispensing thereof, for example in a small amount or as a continuous stream. To do this, the container has a conduit 4 for pressurised supply of the product, on which conduit the dispensing module is mounted, placing a supply passage 5 of the retrieval path 2 in communication with the reservoir 1.

In the embodiments shown, the container has a flexible body 6 that is surmounted by a head 7 forming a supply conduit 4 in which the dispensing module is mounted, said module being supplied with pressurised product by reversible manual deformation of the body 6 of the reservoir 1. In particular, the dispensing module closes off the head 7, allowing dispensing of the product only by means of the retrieval path 2, the external dimensions of said module being able to be substantially similar to the internal dimensions of said head.

In the embodiments shown, the container is in the form of a tube composed of a flexible skirt 6 surmounted by a head 7, said head having a neck in which the supply conduit 4 is formed and a shoulder 7a connecting said neck to the flexible skirt 6.

The flexible skirt 6 is in general formed by a multilayer film that is wound around itself, said skirt also being able to be obtained by extrusion by means of which a hollow cylinder emerges from the extruding machine and is cut to the desired dimensions in order to form the skirt 6.

The tube head 7 can be moulded by injection directly on the skirt 6, and the mould is then in the shape of the head 7 to be moulded and the upper end of the skirt 6 on which the material of the head 7 will be overmoulded, or moulded separately by injection. In the latter case, the tube head 7 is fixed to the skirt 6 by thermal welding.

According to another embodiment, the head 7 of the container is equipped with a member for pressurised extraction of the product contained in the reservoir 1, in particular a pump including the means required for pressurising the product to be dispensed by means of a supply conduit. In particular, the supply conduit may be reversibly movable over a stroke for dispensing/suction of the product, said movement being actuated by a dispensing module forming a push button.

In relation to the drawings, the dispensing module comprises a cap 8 that is mounted on a base 9, forming the path 2 therebetween for retrieving the product from a supply passage 5 which is intended to be in communication with the supply conduit 4 to a passage 3 discharging said product for the dispensing thereof, said path having said supply and discharge passages.

In particular, the cap 8 has an aperture 10 opening into an upper wall 11, the base 9 having a needle 12. According to the embodiments in FIGS. 1 to 5, 7 and 8, the free end of the needle 12 is arranged in the aperture 10 in order to form the discharge passage 3 at the interface thereof. In FIG. 6, the discharge passage 3 is equipped with a valve in the form of a ball 40 which is mounted in a seat 41 between a stable state of closure of said passage (FIG. 6a) and a raised state of opening (FIG. 6b) by pressure of the product in order to allow said product to be dispensed through the aperture 10.

Moreover, the base 9 and/or the cap 8 may comprise means for mounting on the conduit 4 for pressurised supply of the product. In the embodiments in FIGS. 1 to 6, the cap 8 has an external surface 13 that is fitted in a ring 14 formed in the neck of the head 7, said surface being surmounted by a radial rim 15 coming into axial abutment on said ring in order to define the end of fitting together. Moreover, the head 7 is provided with an external thread 16 allowing the mounting of a lid for covering the dispensing module between two uses.

Figure 7:
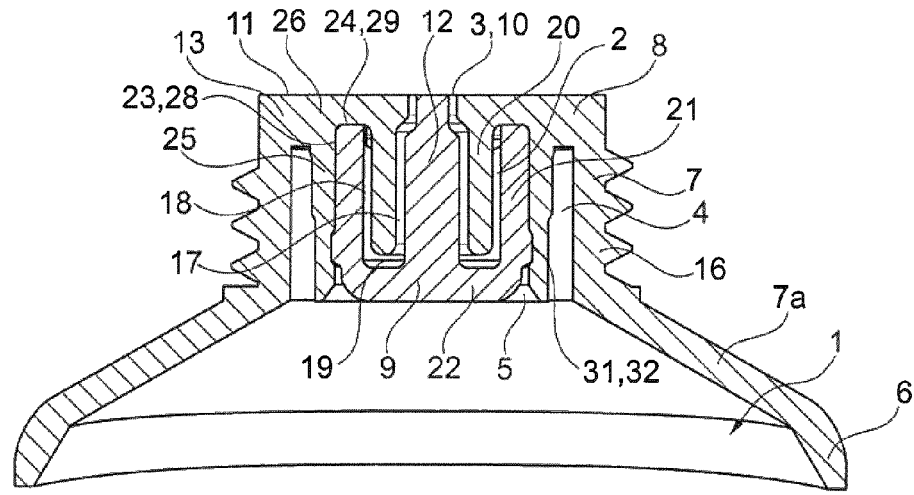
FIG. 7 is a partial longitudinal section of a container according to an embodiment of the invention.
Figure 8:
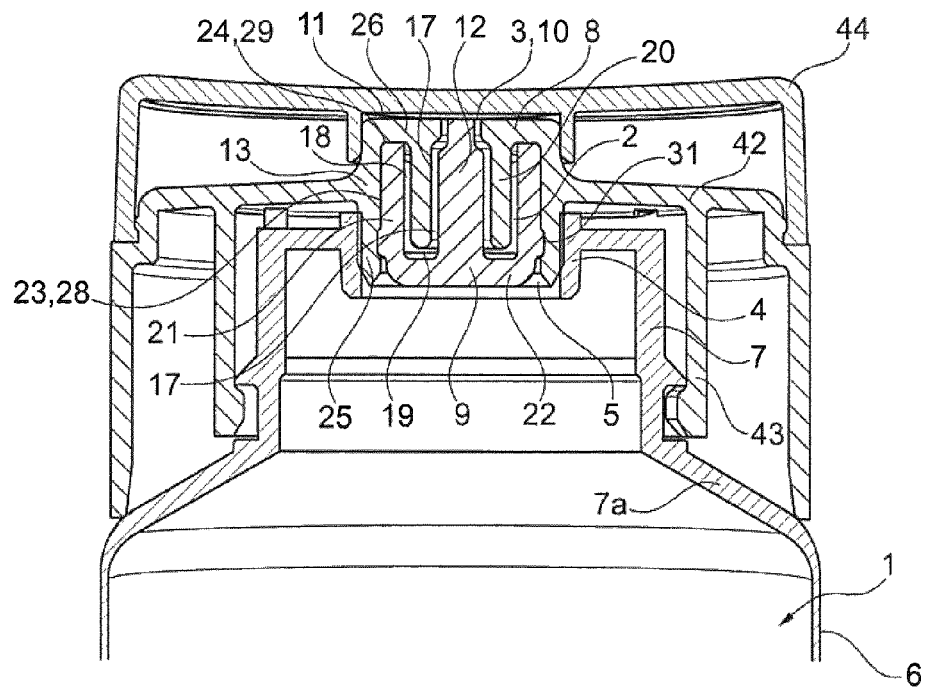
FIG. 8 is a partial longitudinal section of a container according to an embodiment of the invention.

In relation to FIG. 7, the external surface 13 is formed in the neck of the head 7 in order to produce the cap 8 and said head in a single piece. FIG. 8 shows the integration of the cap 8 in a service capsule, the external surface 13 connecting said cap to the sleeve 42 of said capsule in a single piece. In particular, the sleeve 42 has a skirt 43 for snapping around the head 7 and a cover 44 which is mounted on said sleeve between two uses in order to cover the dispensing module.

The retrieval path 2 has at least one downstream conduit 17 that opens into the discharge passage 3 and at least one upstream conduit 18 that is in communication with the supply passage 5. In particular, the upstream 18 and downstream 17 conduits are arranged concentrically with respect to a product discharge axis A, the upstream conduit 18 being arranged around at least part of the downstream conduit 17.

The upstream 18 and downstream 17 conduits have a U-shaped junction 19 that is designed to place said conduits in communication while causing a significant pressure drop in the retrieval path 2. In particular, the pressure drop is designed to limit the phenomenon of the product being sucked back in from the discharge passage 3 to the reservoir 1 as a result of shape memory of the body 6 after the deformation thereof to pressurise the product. Thus the U-shaped junction 19 contributes to the antimicrobial protection between two uses by preventing product which has potentially been contaminated during the dispensing from being introduced into the retrieval path 2 and therefore subsequently being dispensed.

To increase the protection vis-à-vis the risk of contamination of the product by bacteria and fungi, at least one of the upstream 18 and downstream 17 conduits is delimited by at least one wall that is capable of providing microbiocidal action on the product contained in said conduit. Thus, even in the case of a slight suction of product back into the retrieval path 2, said path is decontaminated when it is immobilised between two uses so as to risk neither subsequent dispensing of a dose of contaminated product nor the back-contamination of the product contained in the reservoir 1.

Advantageously, the upper wall 11 of the cap 8 can be capable of providing microbiocidal action on the product arranged thereon between two dispensings, in particular in the form of soiling by spreading of said product on said wall when it is retrieved by the finger of the user.

In particular, provision can be made for the cap 8 and/or the base 9 to be produced from a material having microbiocidal properties in order to delimit at least one conduit 17, 18 with at least one wall which is capable of providing a microbiocidal action, in particular a wall which is arranged in the immediate vicinity of the discharge passage 3 where the risk of introduction of contaminants is greatest. Furthermore, in relation to FIG. 6, the ball 40 can be produced from a material which is capable of providing a microbiocidal action.

The microbiocidal properties of the material can be obtained by diffusing an antimicrobial agent in the product, for example having an organic base such as Trichlosan (a trade name of the company Melcoplast) or having a silver or mineral base. In particular, the material may comprise at least one polyolefin, for example polyethylene, polypropylene and/or polystyrene, which contains at least one antimicrobial agent.

The microbiocidal properties of the material may also be obtained by contact of the product with a microbiostatic agent, for example using a metal material such as a copper or zinc alloy or a material comprising at least one polyolefin containing metal particles of this type or one that has undergone surface treatment by fluoridation, galvanising or copper plating.

The microbiocidal properties of the material may also be obtained by irradiating the product with radiation having a suitable wavelength, in particular by means of a material that has photoluminescent properties after exposure to outside light. In particular, the material may be based on at least one polyolefin containing at least one additive which is capable of emitting photoluminescent radiation that has a wavelength of between 250 and 260 nanometers, and in particular of 254 nanometers, which corresponds to the same order of magnitude as sterilising ultraviolet radiation.

In the embodiments shown, the upper wall 11 is equipped with an inner skirt 20 that extends below the aperture 10 while being arranged around the needle 12 in order to form the downstream conduit 17 at the interface between the internal wall of said inner skirt and the peripheral wall of said needle, the upstream conduit 18 being formed at the interface between the external wall of said skirt and the internal wall of a cavity 21 of the base 9.

Advantageously, the upstream 18 and downstream 17 conduits are each delimited between two walls, the separation of which depends on the viscosity of the product and the sensitivity thereof to microbial contamination, for example being between 0.2 mm and 1 mm, in particular being approximately 0.3 mm.

Thus, by reducing the amount thereof, it is possible to ensure reliable and rapid decontamination of the product contained in the retrieval path 2 between two dispensings. In particular, the microbiocidal action on the product contained in the retrieval path 2 is designed to be quicker than the microbial proliferation towards the reservoir 1, thus stopping the progress thereof.

The U-shaped junction 19 is formed between the free end of the inner skirt 20 and a connection surface 22 between the needle 12 and the cavity 21, the downstream conduit 17 having an ascending direction of flow of the product from the U-shaped junction 19 towards the discharge passage 3, the upstream conduit 18 having a descending direction of flow of said product. The retrieval path 2 thus has a turn by 180° in order to increase the length thereof without having a significant impact on the size of the dispensing module.

Furthermore, the retrieval path 2 has a second upstream conduit 23 by means of which the first upstream conduit 18 is in communication with the supply passage 5. To do this, the supply passage 5 opens into the second upstream conduit 23 and the two upstream conduits 18, 23 are in communication via a U-shaped junction 24, the direction of which is opposite to that of the U-shaped junction 19 placing the upstream 18 and downstream 17 conduits in communication. Thus the length of the retrieval path 2 and therefore the pressure drop in said path are increased further in order to limit even more the possibility of contaminated product being sucked back in.

In the embodiments shown, the upper wall 11 is equipped with an outer skirt 25 extending around the inner skirt 20, the surface 13 being formed on the external wall of said outer skirt. The second upstream conduit 23 is formed at the interface between the external wall of the cavity 21 and the internal wall of the outer skirt 25, the second U-shaped junction 24 being formed between the free end of the cavity 21 and a connecting surface 26 between said skirts.

Figure 5:
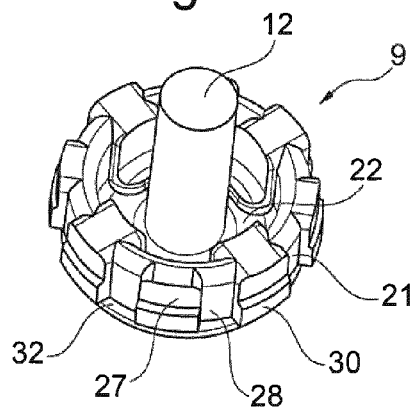
FIG. 5 shows a base of a dispensing module according to a variant of the invention, FIG. 5a being a partial longitudinal section of a container equipped with a dispensing module comprising said base.
Figure 5A:
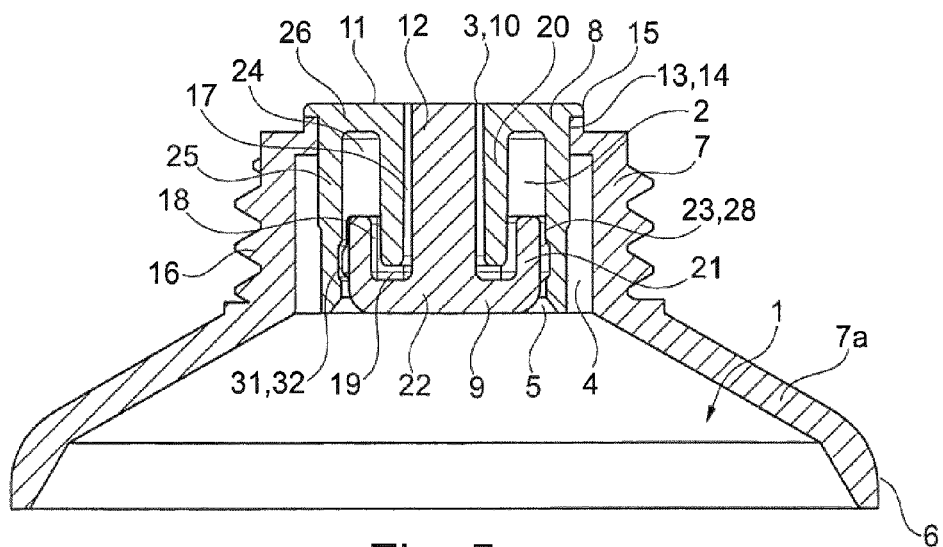
Figure 6A:
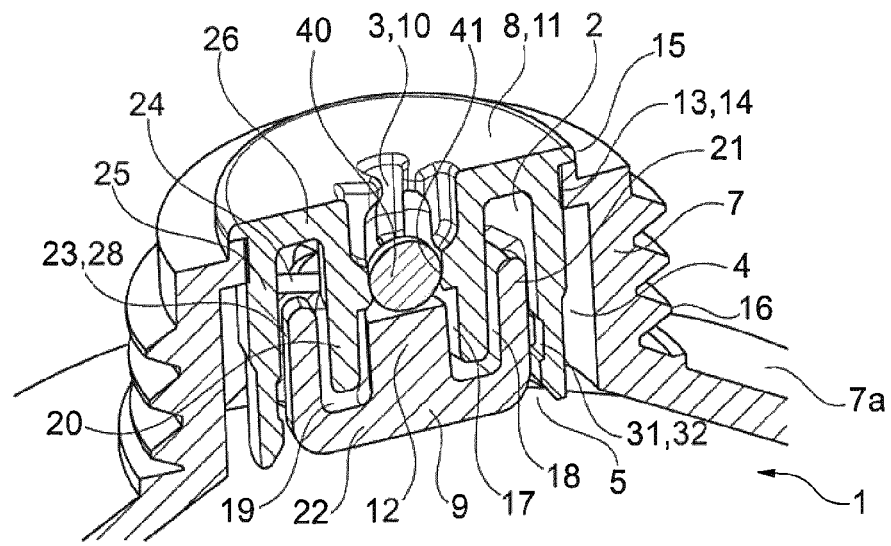
FIG. 6 are cut-away perspective views of a container according to an embodiment of the invention in which the dispensing module is in the closed state (FIG. 6a) and in the open state (FIG. 6b) respectively.
Figure 6B:
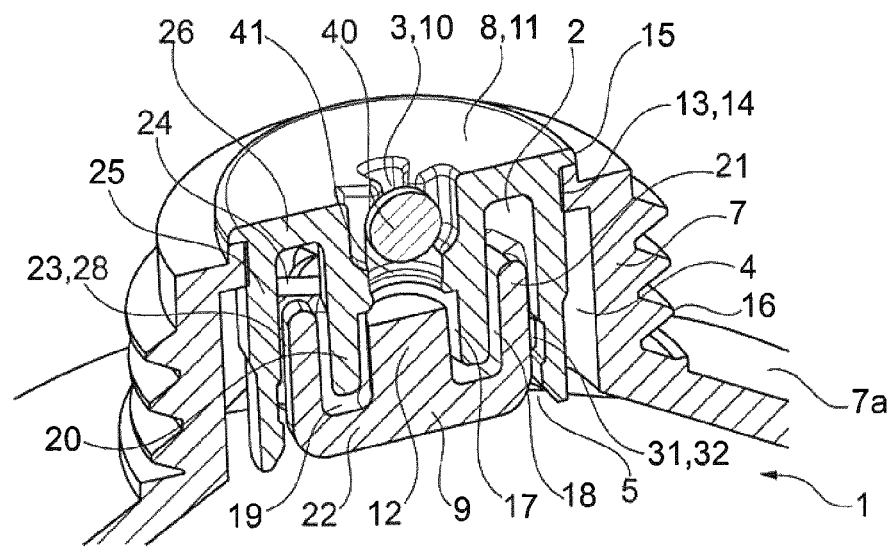

In relation to FIGS. 5 and 6, the axial dimension of the cavity 21 is less than that of the needle 12 and of the skirts 20, 25 in order to increase the amount of product contained at the U-shaped junction 24. Thus the phenomenon of the product being sucked back in is limited by forming a buffer reservoir in the retrieval path 2 between the discharge passage 3 and the reservoir 1, the product contained in said reservoir then being able to be decontaminated between two uses.

The external wall of the cavity 21 is equipped with axial protrusions 27 that are in abutment on the internal wall of the outer skirt 25 in order to ensure controlled separation between the walls delimiting the second upstream conduit 23. Furthermore, sectors 28 for flow of the product in the second upstream conduit 23 are formed between the protrusions 27. Thus the second upstream conduit 23 is angularly discontinuous in order to limit the volume thereof.

Moreover, the protrusions 27 bear ledges 30 for snapping the base 9 into a groove 31 which is formed in the internal wall of the outer skirt 25, forming therebetween sectors 32 supplying product to the second upstream conduit 23.

In relation to FIGS. 1 to 4, 7 and 8, the protrusions 27 extend over the free end of the cavity 21 while being in abutment on the surface 26 in order to form sectors 29 for flow of the product in the second U-shaped junction 24.

Figure 2A:
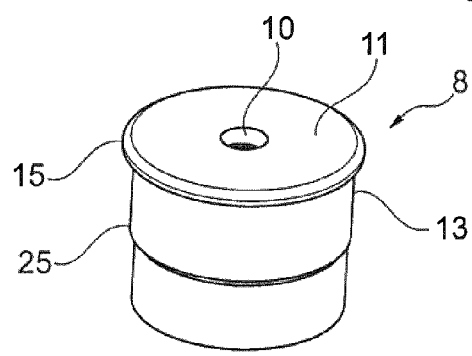
FIG. 2 show the cap of the dispensing module of the container in FIG. 1, in a side perspective view (FIG. 2a) and a perspective view from below (FIG. 2b) respectively.
Figure 2B:
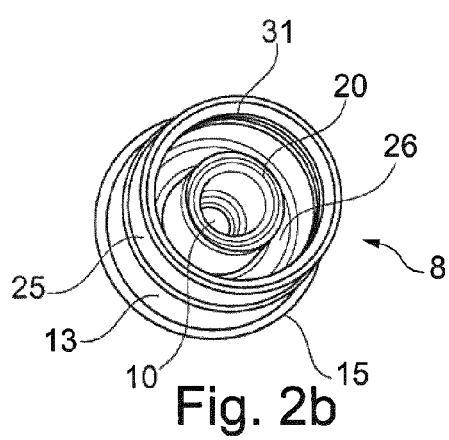
Figure 3A:
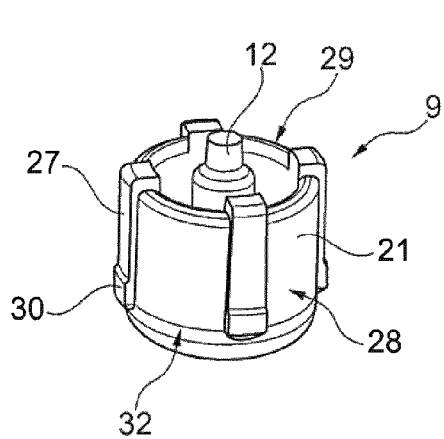
FIG. 3 show the base of the dispensing module of the container in FIG. 1, in a side perspective view (FIG. 3a) and a perspective view from above (FIG. 3b) respectively.
Figure 3B:
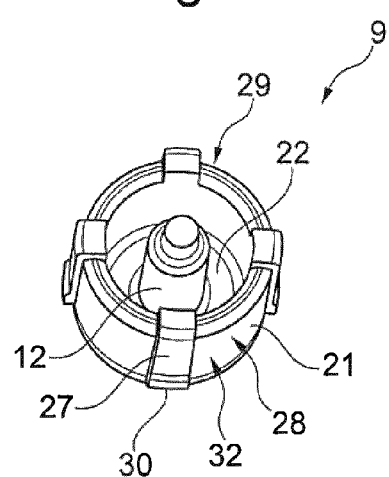

In FIGS. 1 to 3, the first upstream conduit 18 and the downstream conduit 17 are annular and each have a diameter that is less than the diameter of the second upstream conduit 23.

Figure 4:
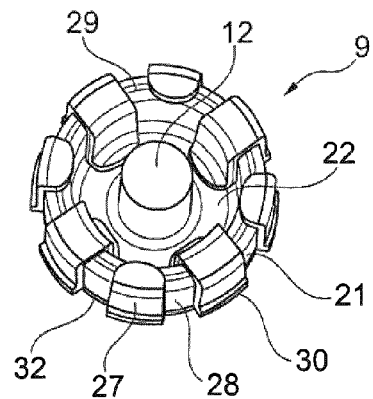
FIG. 4 shows a base of a dispensing module according to a variant of the invention.

In relation to FIGS. 4 and 5, the first upstream conduit 18 may be angularly discontinuous by providing that at least some protrusions 27 extend over the internal wall of the cavity 21. In particular, it is then possible to vary the relative cross sections of the upstream channels 18, 23 in order to optimise the pressure drop in the retrieval path 2, in particular by providing, as shown, that only one protrusion 27 out of two extends over the internal wall of the cavity 21.

The invention claimed is:

1. Module for dispensing a product, configured to be mounted on a supply conduit for pressurised supply of said product,
    said module having a retrieval path for retrieving the product from a supply passage communicating with said supply conduit to a discharge passage for discharging said product for the dispensing thereof, a cap that is mounted on a base, forming therebetween the retrieval path having the supply and discharge passages,
    wherein said retrieval path has at least one downstream conduit that opens into the discharge passage and at least one upstream conduit that is in communication with the supply passage wherein the upstream and downstream conduits are approximately the same length,
    said module comprising a U-shaped junction placing the upstream and downstream conduits in communication with each other, at least one of said upstream and downstream conduits being delimited by at least one wall that provides a microbiocidal action on the product contained in said conduit, wherein the microbiocidal action is produced from at least one material having microbiocidal properties by diffusion of an antimicrobial agent, by contact with a microbiostatic agent, and/or by admitting irradiation.

2. Dispensing Module according to claim 1, wherein the downstream conduit has an ascending direction of flow of the product from the U-shaped junction towards the discharge passage, the upstream conduit having a descending direction of flow of said product.

3. Dispensing Module according to claim 1, wherein the upstream and downstream conduits are arranged concentrically with respect to a product discharge axis (A).

4. Dispensing Module according to claim 1, wherein the upstream conduit is arranged around at least part of the downstream conduit.

5. Dispensing Module according to claim 1, wherein the retrieval path has a second upstream conduit into which the supply passage opens, the two upstream conduits being in communication via a U-shaped junction, the direction of which is opposite to that of the U-shaped junction placing the upstream and downstream conduits in communication.

6. Dispensing Module according to claim 1, wherein the cap has an aperture opening into a wall, the base having a needle, the free end of which is arranged in said aperture in order to form the discharge passage.

7. Dispensing Module according to claim 6, wherein the wall is equipped with an inner skirt that extends under the aperture while being arranged around the needle in order to form the downstream conduit at the interface between the internal wall of said inner skirt and the peripheral wall of said needle, the upstream conduit being formed at the interface between the external wall of said skirt and the internal wall of a cavity of the base, the U-shaped junction being formed between the free end of the inner skirt and a connecting surface between said needle and said cavity.

8. Dispensing Module according to claim 7, wherein the wall is equipped with an outer skirt extending around the inner skirt, the second upstream conduit being formed at the interface between an external wall of the cavity and the internal wall of the outer skirt, the second U-shaped junction being formed between the free end of the cavity and a connecting surface between said skirts.

9. Dispensing Module according to claim 8, wherein the external wall of the cavity is equipped with axial protrusions that are in abutment on the internal wall of the outer skirt, forming therebetween sectors for flow of the product in the second upstream conduit.

10. Dispensing Module according to claim 9, wherein the protrusions bear ledges for snapping the base into the cap.

11. Dispensing Module according to claim 1, wherein the discharge passage opens into a wall that provides said microbiocidal action on the product arranged on said wall between two dispensings.

12. Container comprising a reservoir configured to package a product, said container having a supply conduit for pressurised supply of said product and, mounted on said conduit, a dispensing module according to claim 1.

13. Container according to claim 12, wherein the container is in the form of a tube composed of a flexible skirt surmounted by a head, said head having a neck in which the supply conduit is formed and a shoulder connecting said neck to the flexible skirt.

* * * * *